United States Patent
El-Lateef Ahmed et al.

(10) Patent No.: US 11,987,578 B1
(45) Date of Patent: May 21, 2024

(54) 7-(4-((5-(2-CHLOROBENZYLIDENEAMINO)-2-THIOXO-1,3,4-THIADIAZOL-3(2H)-YL)METHYL)PIPERAZIN-1-YL)-1-CYCLOPROPYL-6-FLUORO-4-OXO-1,4-DIHYDROQUINOLINE-3-CARBOXYLIC ACID AS AN ANTI-INFLAMMATORY COMPOUND

(71) Applicant: KING FAISAL UNIVERSITY, Al-Ahsa (SA)

(72) Inventors: Hany Mohamed Abd El-Lateef Ahmed, Al-Ahsa (SA); Mai Mostafa Khalaf Ali, Al-Ahsa (SA); Antar Ahmed Abdelhamid Ahmed, Sohag (EG); Amer A. Amer, Sohag (EG)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/434,601

(22) Filed: Feb. 6, 2024

Related U.S. Application Data

(62) Division of application No. 18/369,782, filed on Sep. 18, 2023.

(51) Int. Cl.
  *C07D 417/12* (2006.01)
  *A61P 29/00* (2006.01)
(52) U.S. Cl.
  CPC ............ *C07D 417/12* (2013.01); *A61P 29/00* (2018.01)
(58) Field of Classification Search
  CPC .................................................. C07D 417/12
  See application file for complete search history.

(56) References Cited

PUBLICATIONS

Ragab, Fatma A., et al. "Synthesis of novel thiadiazole derivatives as selective COX-2 inhibitors." MedChemComm 7.12 (2016): 2309-2327.
Mohammed, Hamada HH, et al. "Synthesis, molecular docking, antimicrobial evaluation, and DNA cleavage assay of new thiadiazole/oxadiazole ciprofloxacin derivatives." Monatshefte für Chemie-Chemical Monthly 150 (2019): 1809-1824.
Zaher, Nashwa H., et al. "Potential effect of novel thiadiazole derivatives against radiation induced inflammation with low cardiovascular risk in rats." Medicinal Chemistry Research 31.11 (2022): 1875-1888.
Zusso, Morena, et al. "Ciprofloxacin and levofloxacin attenuate microglia inflammatory response via TLR4/NF-KB pathway." Journal of neuroinflammation 16.1 (2019): 1-12.
Ahadi, Hamideh, et al. "Synthesis and biological assessment of ciprofloxacin-derived 1, 3, 4-thiadiazoles as anticancer agents." Bioorganic Chemistry 105 (2020): 104383.
Sachse, F., et al. "Anti-inflammatory effects of ciprofloxacin in *S. aureus* Newman induced nasal inflammation in vitro." Journal of inflammation 5.1 (2008): 1-6.
Lahat, Guy, et al. "Immunomodulatory effects of ciprofloxacin in TNBS-induced colitis in mice." Inflammatory bowel diseases 13.5 (2007): 557-565.
Akhtar, Rabia, et al. "Synthesis of ciprofloxacin-based compounds: A review." Synthetic Communications 46.23 (2016): 1849-1879.

*Primary Examiner* — Brian E McDowell
(74) *Attorney, Agent, or Firm* — Nath, Goldberg & Meyer; Richard C. Litman

(57) ABSTRACT

A 7-(4-((5-(2-chlorobenzylideneamino)-2-thioxo-1,3,4-thiadiazol-3(2H)-yl)methyl)piperazin-1-yl)-1-cyclopropyl-6-fluoro-4-oxo-1,4-dihydroquinoline-3-carboxylic acid compound, its synthesis, and its use as an anticancer and/or anti-inflammatory agent.

1 Claim, 2 Drawing Sheets

7-(4-((5-(2-CHLOROBENZYLIDENEAMINO)-2-THIOXO-1,3,4-THIADIAZOL-3(2H)-YL)METHYL)PIPERAZIN-1-YL)-1-CYCLOPROPYL-6-FLUORO-4-OXO-1,4-DIHYDROQUINOLINE-3-CARBOXYLIC ACID AS AN ANTI-INFLAMMATORY COMPOUND

CROSS-REFERENCE TO RELATED APPLICATION

This application is a divisional of U.S. patent application Ser. No. 18/369,782, filed on Sep. 18, 2023, the entire contents of which are incorporated herein by reference.

BACKGROUND

1. Field

The present disclosure relates to the compound 7-(4-((5-(2-chlorobenzylideneamino)-2-thioxo-1,3,4-thiadiazol-3(2H)-yl)methyl)piperazin-1-yl)-1-cyclopropyl-6-fluoro-4-oxo-1,4-dihydroquinoline-3-carboxylic acid, its synthesis, and its use as an anti-inflammatory and/or anticancer agent.

2. Description of the Related Art

The investigation of organic compounds for drug discovery has been a rapidly emerging theme in medicinal chemistry. For example, due to the enhanced global encumbrance of cancer in the last decades, extensive research has been devoted to discovering novel selective potent candidates with the promising ability to either destroy cancer cells or limit their proliferation.

Similarly, bacterial infection remains a significant threat to human life due to its increasing resistance to conventional antibiotics, which is a growing public health concern. As a result, there is a critical need to create new antimicrobial agents with potent anti-drug-resistant microorganism activity, as well as associated anti-inflammatory activities.

The chemistry of heterocycles lies at the heart of drug discovery. For example, the thiadiazole ring system has shown numerous biological activities including anticancer, antifungal, antiviral, antidiabetic, analgesic, antiepileptic, antibacterial, and anti-inflammatory activities. The enhanced liposolubility imparted by the sulfur atom of the thiadiazole core, in addition to its mesoionic nature, allows such compounds to interact with biological targets with distinct affinities after penetration across cellular membranes. Recent studies have demonstrated the ability of 1,3,4-thiadiazole compounds to inhibit a variety of molecular targets, including kinases, which enables their activity against different cancer cell lines, presenting them as a promising scaffold for antitumor drug discovery.

Furthermore, ciprofloxacin is an antibiotic agent and its derivatives have exhibited diverse biological activities, such as antibacterial, anti-tuberculosis, antifungal, anti-HIV, anti-malarial, anti-tumor, anti-ischemic, and anti-oxidation activities, as well as inhibitory urease activity. Various imaging profiles have been developed in the last years, and the antibacterial properties of ciprofloxacin derivatives have been studied accordingly.

Further, multi-component reactions (MCRs) are economically and environmentally beneficial to industry and have attracted much attention.

Thus, new molecules having desired therapeutic activities and solving the aforementioned problems are desired.

SUMMARY

The present subject matter relates to the synthesis of 1,3,4-thiadiazole derivative "drug-like" substances having biological activity, as well as such synthesized compounds themselves. Hence, herein the present subject matter relates to synthesis of 7-(4-((5-(2-chlorobenzylideneamino)-2-thioxo-1,3,4-thiadiazol-3(2H)-yl)methyl)piperazin-1-yl)-1-cyclopropyl-6-fluoro-4-oxo-1,4-dihydroquinoline-3-carboxylic acid (IV) via a one-pot three-component reaction of 5-(2-chlorobenzylideneamino)-1,3,4-thiadiazole-2(3H)-thione I, formaldehyde II, and ciprofloxacin III in ethanol. This synthesized product is likely to have high anti-inflammatory activity.

In an embodiment, the present subject matter relates to a 7-(4-((5-(2-chlorobenzylideneamino)-2-thioxo-1,3,4-thiadiazol-3(2H)-yl)methyl)piperazin-1-yl)-1-cyclopropyl-6-fluoro-4-oxo-1,4-dihydroquinoline-3-carboxylic acid compound having the formula I:

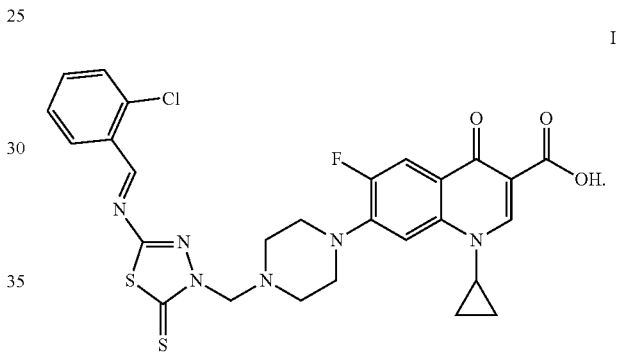

I

In another embodiment, the present subject matter relates to a pharmaceutically acceptable composition comprising a therapeutically effective amount of the 7-(4-((5-(2-chlorobenzylideneamino)-2-thioxo-1,3,4-thiadiazol-3(2H)-yl)methyl)piperazin-1-yl)-1-cyclopropyl-6-fluoro-4-oxo-1,4-dihydroquinoline-3-carboxylic acid compound and a pharmaceutically acceptable carrier.

In an additional embodiment, the present subject matter relates to a method of treating inflammation in a patient comprising administering to a patient in need thereof a therapeutically effective amount of the 7-(4-((5-(2-chlorobenzylideneamino)-2-thioxo-1,3,4-thiadiazol-3(2H)-yl)methyl)piperazin-1-yl)-1-cyclopropyl-6-fluoro-4-oxo-1,4-dihydroquinoline-3-carboxylic acid compound.

In one more embodiment, the present subject matter relates to a method of making the 7-(4-((5-(2-chlorobenzylideneamino)-2-thioxo-1,3,4-thiadiazol-3(2H)-yl)methyl)piperazin-1-yl)-1-cyclopropyl-6-fluoro-4-oxo-1,4-dihydroquinoline-3-carboxylic acid compound, the method comprising: stirring a solution of 5-(2-chlorobenzylideneamino)-1,3,4-thiadiazole-2(3H)-thione and formaldehyde in ethanol to obtain a reaction mixture; adding ciprofloxacin HCl and triethylamine to the reaction mixture and stirring with reflux; cooling the reaction mixture at room temperature to obtain a solid; and obtaining the 7-(4-((5-(2-chlorobenzylideneamino)-2-thioxo-1,3,4-thiadiazol-3(2H)-yl)methyl)piperazin-1-yl)-1-cyclopropyl-6-fluoro-4-oxo-1,4-dihydroquinoline-3-carboxylic acid compound.

These and other features of the present subject matter will become readily apparent upon further review of the following specification.

DETAILED DESCRIPTION OF THE PREFERRED EMBODIMENTS

Figure 1:
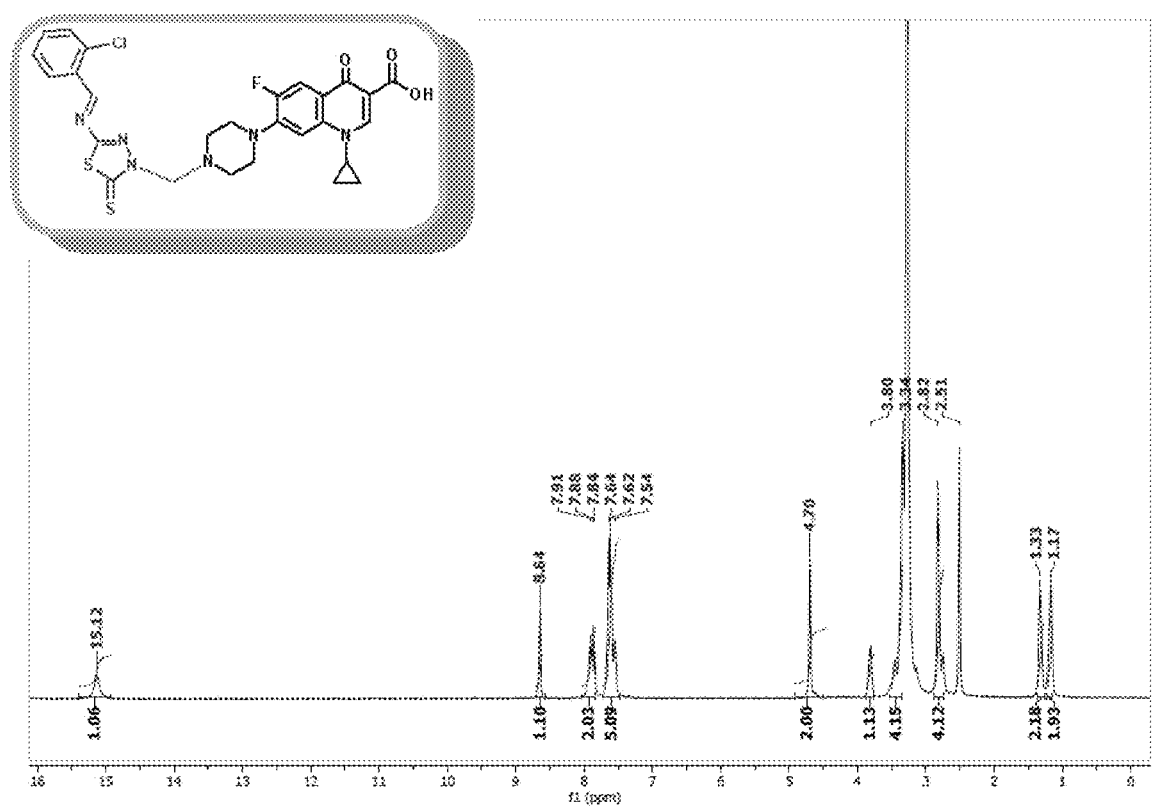
FIG. 1 shows a $^1$H NMR analysis of the 7-(4-((5-(2-chlorobenzylideneamino)-2-thioxo-1,3,4-thiadiazol-3(2H)-yl)methyl)piperazin-1-yl)-1-cyclopropyl-6-fluoro-4-oxo-1,4-dihydroquinoline-3-carboxylic acid compound.

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as inflammation.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to the synthesis of 1,3,4-thiadiazole derivative "drug-like" substances having biological activity, as well as such synthesized compounds themselves. Hence, herein the present subject matter relates to synthesis of 7-(4-((5-(2-chlorobenzylideneamino)-2-thioxo-1,3,4-thiadiazol-3(2H)-yl)methyl)piperazin-1-yl)-1-cyclopropyl-6-fluoro-4-oxo-1,4-dihydroquinoline-3-carboxylic acid (IV) via a one-pot three-component reaction of 5-(2-chlorobenzylideneamino)-1,3,4-thiadiazole-2(3H)-thione I. formaldehyde II, and ciprofloxacin III in ethanol. This synthesized product is likely to have high anti-inflammatory activity.

In an embodiment, the present subject matter relates to a 7-(4-((5-(2-chlorobenzylideneamino)-2-thioxo-1,3,4-thiadiazol-3(2H)-yl)methyl)piperazin-1-yl)-1-cyclopropyl-6- fluoro-4-oxo-1,4-dihydroquinoline-3-carboxylic acid compound having the formula I:

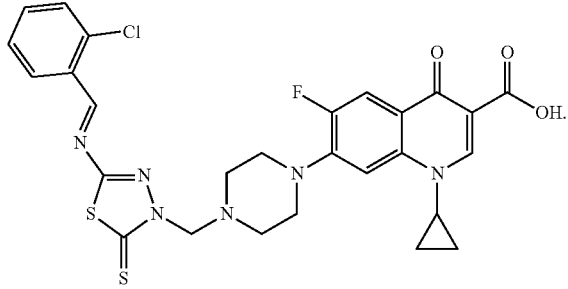

In certain embodiments, the 7-(4-((5-(2-chlorobenzylideneamino)-2-thioxo-1,3,4-thiadiazol-3(2H)-yl)methyl)piperazin-1-yl)-1-cyclopropyl-6-fluoro-4-oxo-1,4-dihydroquinoline-3-carboxylic acid compound can be obtained as crystals. In further embodiments, the 7-(4-((5-(2-chlorobenzylideneamino)-2-thioxo-1,3,4-thiadiazol-3(2H)-yl)methyl)piperazin-1-yl)-1-cyclopropyl-6-fluoro-4-oxo-1,4-dihydroquinoline-3-carboxylic acid compound can have a melting point of about 207° C. to about 209° C.

In another embodiment, the present subject matter relates to a pharmaceutically acceptable composition comprising a therapeutically effective amount of the 7-(4-((5-(2-chlorobenzylideneamino)-2-thioxo-1,3,4-thiadiazol-3(2H)-yl)methyl)piperazin-1-yl)-1-cyclopropyl-6-fluoro-4-oxo-1,4-dihydroquinoline-3-carboxylic acid compound and a pharmaceutically acceptable carrier.

In this regard, the present subject matter is further directed to pharmaceutical compositions comprising a therapeutically effective amount of the compound as described herein together with one or more pharmaceutically acceptable carriers, excipients, or vehicles. In some embodiments, the present compositions can be used for combination therapy, where other therapeutic and/or prophylactic ingredients can be included therein.

The present subject matter further relates to a pharmaceutical composition, which comprises a present compound together with at least one pharmaceutically acceptable auxiliary.

Non-limiting examples of suitable excipients, carriers, or vehicles useful herein include liquids such as water, saline, glycerol, polyethylene glycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compound is typically administered at a therapeutically or pharmaceutically effective dosage, e.g., a dosage sufficient to provide treatment for inflammation. Administration of the compound or pharmaceutical compositions thereof can be by any method that delivers the compound systemically and/or locally. These methods include oral routes, parenteral routes, intraduodenal routes, and the like.

While human dosage levels have yet to be optimized for the present compound, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present compound for treatment of cancer or inflammation, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present compounds can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

The present compounds may also be administered as compositions prepared as foods for humans or animals, including medical foods, functional food, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of the present compound, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium croscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinyl pyrrolidine, gelatin, cellulose, and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrin derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium croscarmellose, glucose, sucrose, magnesium carbonate, sodium saccharin, talcum, and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly, or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol, or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compound contained in such parenteral compositions is highly dependent on the specific nature thereof, as well as the activity of the compound and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example less than 10 microns.

In an additional embodiment, the present subject matter relates to a method of treating inflammation in a patient comprising administering to a patient in need thereof a therapeutically effective amount of the 7-(4-((5-(2-chlorobenzylideneamino)-2-thioxo-1,3,4-thiadiazol-3(2H)-yl)methyl)piperazin-1-yl)-1-cyclopropyl-6-fluoro-4-oxo-1,4-dihydroquinoline-3-carboxylic acid compound.

In one more embodiment, the present subject matter relates to a method of making the 7-(4-((5-(2-chlorobenzylideneamino)-2-thioxo-1,3,4-thiadiazol-3(2H)-yl)methyl)piperazin-1-yl)-1-cyclopropyl-6-fluoro-4-oxo-1,4-dihydroquinoline-3-carboxylic acid compound, the method comprising: stirring a solution of 5-(2-chlorobenzylideneamino)-1,3,4-thiadiazole-2(3H)-thione and formaldehyde in ethanol to obtain a reaction mixture; adding ciprofloxacin HCl and triethylamine to the reaction mixture and stirring with reflux; cooling the reaction mixture at room temperature to obtain a solid; and obtaining the 7-(4-((5-(2-chlorobenzylideneamino)-2-thioxo-1,3,4-thiadiazol-3(2H)-yl)methyl)piperazin-1-yl)-1-cyclopropyl-6-fluoro-4-oxo-1,4-dihydroquinoline-3-carboxylic acid compound.

The present production methods can be further seen by referring to the following Scheme 1:

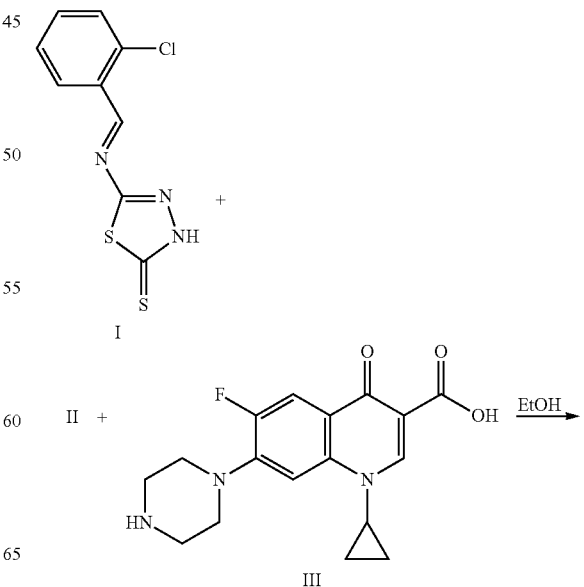

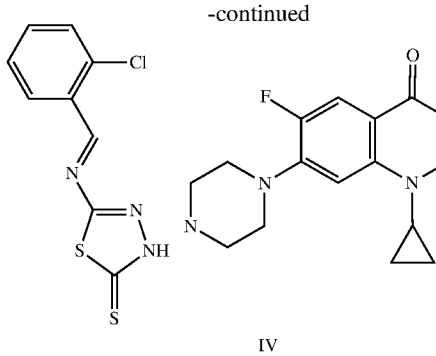

IV

In an embodiment of the present production methods, the reaction mixture can be stirred at room temperature for at least about 55 minutes before the adding of the ciprofloxacin HCl and triethylamine.

In another embodiment of the present production methods, after the adding of the ciprofloxacin HCl and triethylamine, the reaction mixture can be stirred for at least about 2 hours.

In a further embodiment of the present production methods, the solid can be collected by filtration, washed with water, and recrystallized from ethanol to obtain the 7-(4-((5-(2-chlorobenzylideneamino)-2-thioxo-1,3,4-thiadiazol-3(2H)-yl)methyl)piperazin-1-yl)-1-cyclopropyl-6-fluoro-4-oxo-1,4-dihydroquinoline-3-carboxylic acid compound.

In an embodiment of the present production methods, the 5-(2-chlorobenzylideneamino)-1,3,4-thiadiazole-2(3H)-thione and formaldehyde can be added in an about 3:7 molar ratio. Similarly, the ciprofloxacin HCl and triethylamine can be added in an about 3:4 molar ratio. Likewise, the 5-(2-chlorobenzylideneamino)-1,3,4-thiadiazole-2(3H)-thione, formaldehyde, ciprofloxacin HCl, and triethylamine can be added in an about 3:7:3:4 molar ratio.

In an additional embodiment of the present production methods, the 7-(4-((5-(2-chlorobenzylideneamino)-2-thioxo-1,3,4-thiadiazol-3(2H)-yl)methyl)piperazin-1-yl)-1-cyclopropyl-6-fluoro-4-oxo-1,4-dihydroquinoline-3-carboxylic acid compound can be obtained in an about 73% yield.

The following examples relate to various methods of manufacturing the specific compounds and application of the same, as described herein. All compound numbers expressed herein are with reference to the synthetic pathway figures shown above.

EXAMPLES

Example 1

Preparation of 7-(4-((5-(2-chlorobenzylideneamino)-2-thioxo-1,3,4-thiadiazol-3(2H)-yl)methyl)piperazin-1-yl)-1-cyclopropyl-6-fluoro-4-oxo-1,4-dihydroquinoline-3-carboxylic acid A solution of 5-(2-chlorobenzylideneamino)-1,3,4-thiadiazole-2(3H)-thione (0.77 g, 0.003 mol) and formaldehyde (0.2 g, 0.007 mol) was stirred in 70 ml ethanol for 55 min, then ciprofloxacin HCL (1.28 g. 0.003 mol), and triethylamine (0.100 g, 0.004 mol) was added, and the reaction mixture was stirred with reflux for 2 h. The reaction mixture was allowed to cool at room temperature, the separated solid was filtered off, washed with water, and recrystallized from ethanol to give the desired product 7-(4-((5-(2-chlorobenzylideneamino)-2-thioxo-1,3,4-thiadiazol-3(2H)-yl)methyl)piperazin-1-yl)-1-cyclopropyl-6-fluoro-4-oxo-1,4-dihydroquinoline-3-carboxylic acid (IV).

Figure 2:
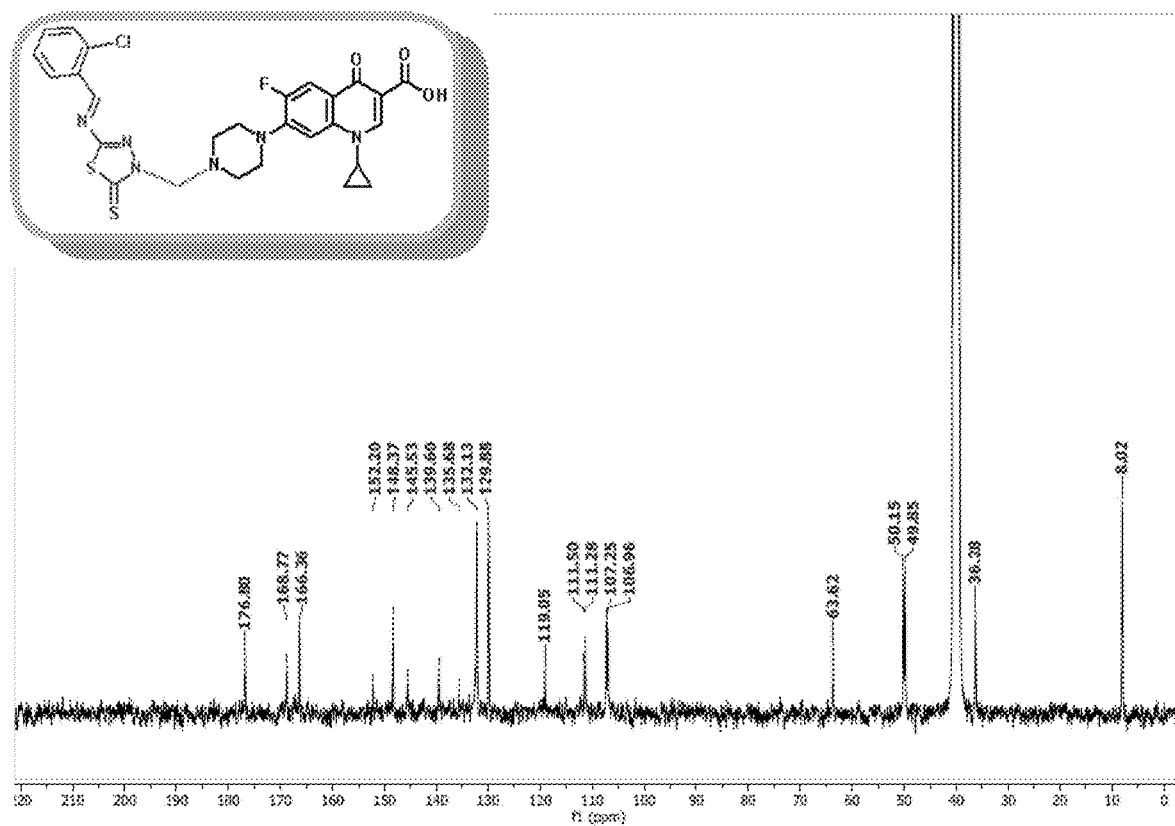
FIG. 2 shows a $^{13}$C NMR analysis of the 7-(4-((5-(2-chlorobenzylideneamino)-2-thioxo-1,3,4-thiadiazol-3(2H)-yl)methyl)piperazin-1-yl)-1-cyclopropyl-6-fluoro-4-oxo-1,4-dihydroquinoline-3-carboxylic acid compound.

Characterization of the prepared compound using $^1$H NMR, and $^{13}$C NMR analysis is shown in FIGS. 1-2, respectively. The elemental analysis can be seen as follows.

7-(4-((5-(2-chlorobenzylideneamino)-2-thioxo-1,3,4-thiadiazol-3(2H)-yl)methyl)piperazin-1-yl)-1-cyclopropyl-6-fluoro-4-oxo-1,4-dihydroquinoline-3-carboxylic acid (IV)

Mp. 207-209° C. Yield=73%. FTIR (KBr, cm$^{-1}$) 3369 (OH), 3035 (CHarom.), 2940, 2851 (CHaliph.), 1728 and 1710 (C=O). $^1$H-NMR (DMSO-d6/D$_2$O, 400 MHz): 15.12 (br. s, OH, COOH), 8.64 (s, 1H, CH=N), 7.91-7.84 (m, 2H, CHarom), 7.64-7.54 (m, 5H, CHarom.), 4.70 (s, 2H, N—CH$_2$), 3.80 (br. s., 1H, CH cyclopropyl), 3.34 (m, 4H, 2 N—CH$_2$), 2.82 (m, 4H, 2 N—CH$_2$), 1.33 (s, 2H, CH$_2$cyclopropyl), 1.17 (br. s, 2H, CH$_2$cyclopropyl); $^{13}$C NMR (100 MHz, DMSO-d6/D$_2$O): δ 176.80, 168.77, 166.36, 152.20, 148.37, 145.53, 139.60, 135.68, 132.13, 129.88, 119.05, 111.50, 111.28, 107.25, 106.96, 63.62, 50.15, 49.85, 36.28, 8.02. Analysis: calculated for $C_{27}H_{24}ClFN_6O_8S_2$ (599.10): C, 54.13; H, 4.04; N, 14.03%. Found: C, 54.27; H, 3.97; N, 14.11%.

Example 2

Anti-Inflammatory Activity

Bovine Serum Albumin Assay (BSA)

In vitro-inflammatory activities of the tested samples were determined using a modified method of the BSA assay reported by Williams et al. BSA solution (0.4%, w/v) was prepared in Tris Buffered Saline. The pH was adjusted to 6.4 with glacial acetic acid. Different dilutions of 20, 40, 60, 80, and 100 µg/mL of 7-(4-((5-(2-chlorobenzylideneamino)-2-thioxo-1,3,4-thiadiazol-3(2H)-yl)methyl)piperazin-1-yl)-1-cyclopropyl-6-fluoro-4-oxo-1,4-dihydroquinoline-3-carboxylic acid stock solutions were added to test tubes containing 1 mL of 0.4%, w/v BSA buffer solution. Both negative (solvent) and positive (aspirin) controls were assayed in a similar manner. The solutions were then heated in a water bath at 72° C. for 10 minutes and cooled for 20 minutes under laboratory conditions. The turbidity of the solutions (level of protein precipitation) was measured at 660 nm in Spectrophotometer (V-770 UV-Visible/NIR Spectrophotometer).

The percentage inhibition of precipitation (protein denaturation) was determined relative to the negative control using the following equation:

$$\% \text{ Anti-Denaturation Activity} = \frac{\text{Absorbance of control} - \text{Absorbance of sample} \times 100}{\text{Absorbance of control}}$$

% Anti-Denaturation Activity = % Inhibition of Protein Denaturation = % Anti-inflammatory Activity The in vitro anti-inflammatory activity study of 7-(4-((5-(2-chlorobenzylideneamino)-2-thioxo-1,3,4-thiadiazol-3(2H)-yl)methyl)piperazin-1-yl)-1-cyclopropyl-6-fluoro-4-oxo-1,4-dihydroquinoline-3-carboxylic acid showed that the synthesized compound 7-(4-((5-(2-chlorobenzylideneamino)-2-thioxo-1,3,4-thiadiazol-3(2H)-yl)methyl)piperazin-1-yl)-1-cyclopropyl-6-fluoro-4-oxo-1,4-dihydroquinoline-3-carboxylic acid demonstrated a considerable anti-inflammatory effect. While standard aspirin at 100 µg/ml showed 96.75% inhibition, the present 7-(4-((5-(2-chlorobenzylideneamino)-2-thioxo-1,3,4-thiadiazol-3(2H)-yl)methyl)piperazin-1-yl)-1-cyclopropyl-6-fluoro-4-oxo-1,4-dihydroquinoline-3-carboxylic acid exhibited 90.25% inhibition. Hence the present compound can be used effectively in the management of inflammation.

It is to be understood that the 7-(4-((5-(2-chlorobenzylideneamino)-2-thioxo-1,3,4-thiadiazol-3(2H)-yl)methyl)piperazin-1-yl)-1-cyclopropyl-6-fluoro-4-oxo-1,4-dihydroquinoline-3-carboxylic acid compound, compositions containing the same, and methods of using and producing the same are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of treating inflammation in a patient comprising administering to a patient in need thereof a therapeutically effective amount of 7-(4-((5-(2-chlorobenzylideneamino)-2-thioxo-1,3,4-thiadiazol-3(2H)-yl)methyl) piperazin-1-yl)-1-cyclopropyl-6-fluoro-4-oxo-1,4-dihydroquinoline-3-carboxylic acid.

* * * * *